United States Patent
Schnepp-Pesch et al.

[11] Patent Number: 5,707,386
[45] Date of Patent: Jan. 13, 1998

[54] STENT AND METHOD OF MAKING A STENT

[75] Inventors: Wolfram Schnepp-Pesch; Josef Lindenberg, both of Karlsruhe, Germany

[73] Assignee: Angiomed GmbH & Company Medizintechnik KG, Karlsruhe, Germany

[21] Appl. No.: 495,625
[22] PCT Filed: Jan. 22, 1994
[86] PCT No.: PCT/EP94/00168
§ 371 Date: Sep. 21, 1995
§ 102(e) Date: Sep. 21, 1995
[87] PCT Pub. No.: WO94/17754
PCT Pub. Date: Aug. 18, 1994

[30] Foreign Application Priority Data

Feb. 4, 1993 [DE] Germany ............... 43 03 181.1

[51] Int. Cl.[6] .................................. A61M 29/00
[52] U.S. Cl. .............................. 606/194; 606/191
[58] Field of Search .................. 606/191, 192, 606/194, 198; 623/1, 12; 604/96, 97, 106

[56] References Cited

U.S. PATENT DOCUMENTS

| 5,104,404 | 4/1992 | Wolff. | |
| 5,135,536 | 8/1992 | Hillstead. | |
| 5,158,548 | 10/1992 | Lau et al. | 604/96 |
| 5,421,955 | 6/1995 | Lau et al. | 606/198 |
| 5,514,154 | 5/1996 | Lau et al. | 606/195 |

FOREIGN PATENT DOCUMENTS

| 540290A3 | 5/1993 | European Pat. Off.. |
| 1766921 | 1/1970 | Germany. |

Primary Examiner—Michael Buiz
Assistant Examiner—Kevin Truong
Attorney, Agent, or Firm—Antonelli, Terry, Stout, & Kraus, LLP

[57] ABSTRACT

A stent, which has an easier and better bendability and higher flexibility than known stents, has several meander paths (2,2a,2b,2c) successively arranged in the axial direction (A) and extending over its circumference (U), and between axially facing areas (3,3a,3'a,3b), interconnected by connecting areas (4,4a,4b,4c), of the meander paths (2,2a,2b,2c) in the circumferential direction (U) there are at least two facing, non-interconnected areas (3,3a,3'a,3b) of each meander path (2,2a, 2b,2c).

16 Claims, 3 Drawing Sheets

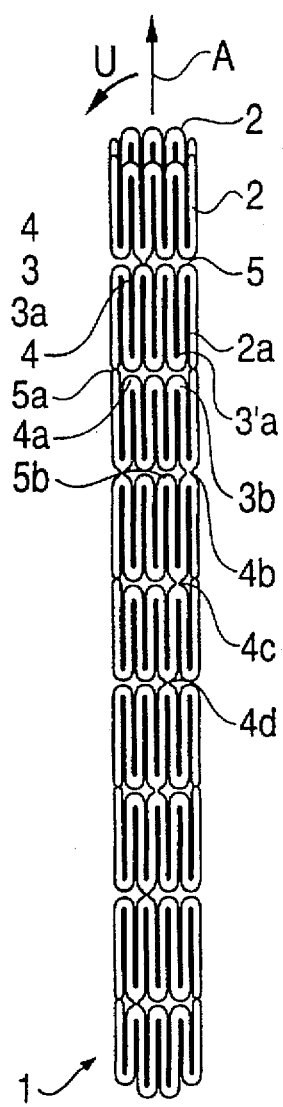
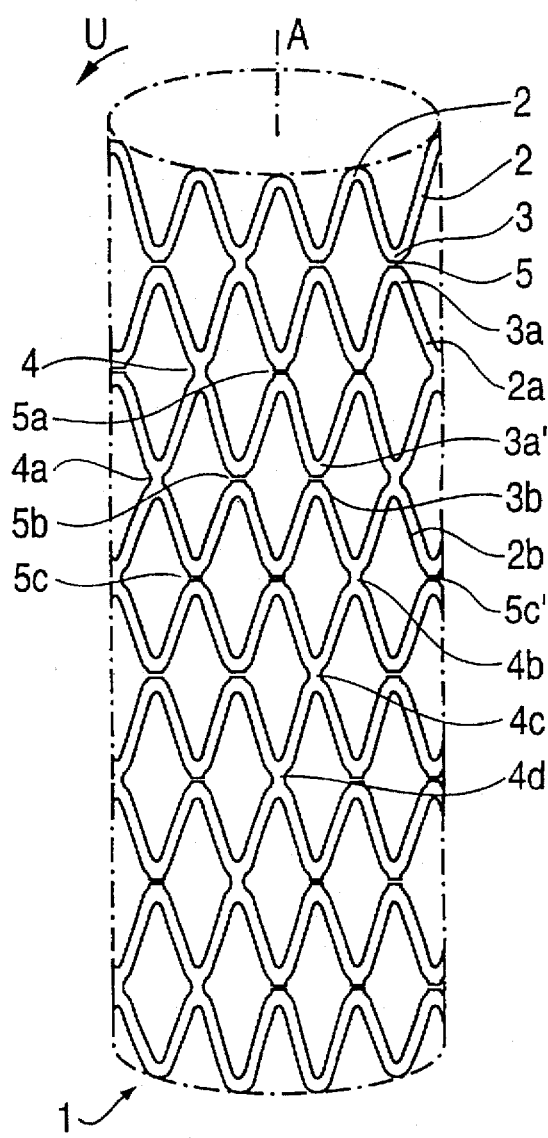

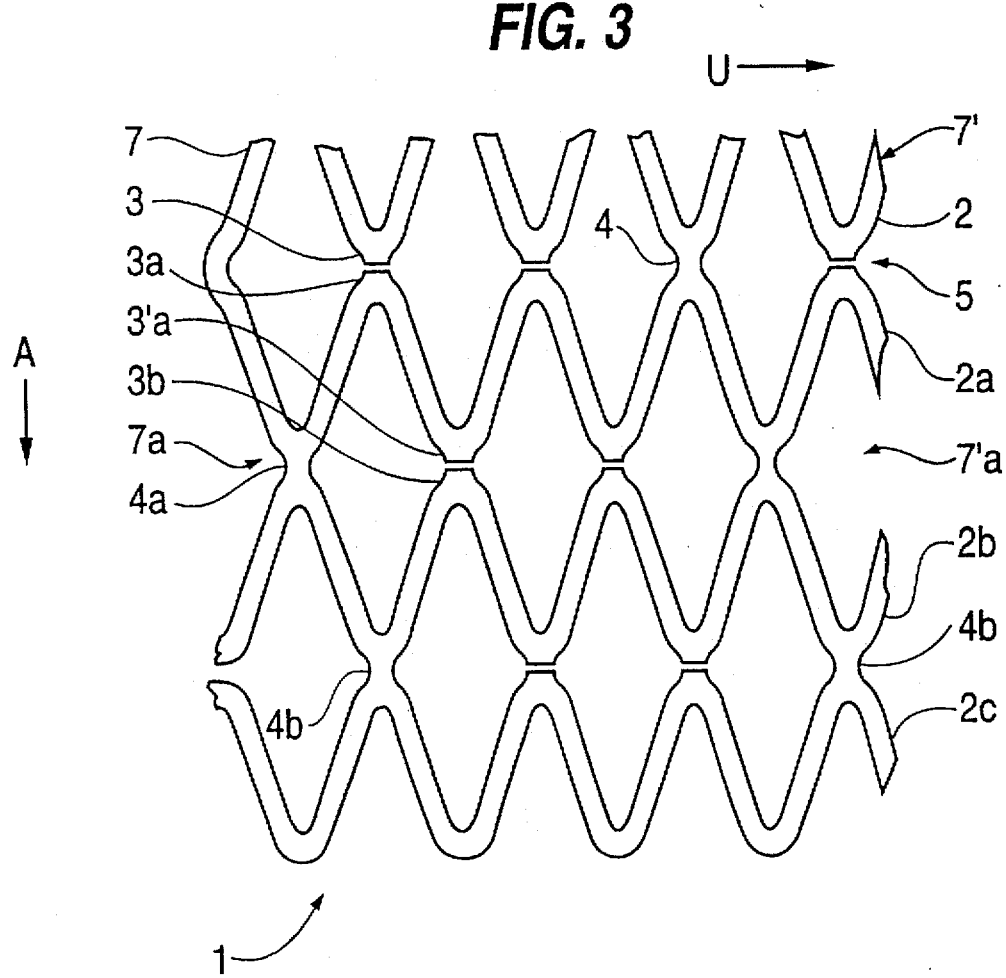

STENT AND METHOD OF MAKING A STENT

FIELD OF THE INVENTION

BACKGROUND OF THE INVENTION

Such stents or implantable catheters, which can be inserted in a body cavity, a vessel or the like, can be made from plastic or an inert metal, such as steel or nickel-titanium alloys. Such stents are in particular known as endovascular or endoluminal stents or intraluminal tubes. The stents are e.g. used for widening the ureter in the prostate region in the case of benign prostate hyperplasia (BPH) or in the case of sclerotic blood vessels for widening and keeping open the same. The stents have material areas and gaps between them. Thus, the parietal tissue of the organ kept open can grow round the stent. Stents can have a spiral construction or can be in the form of a helically wound coil. They can also be made from woven, knitted or braided wire or plastic material. Such stents can have memory characteristics, such as e.g. occur with certain nickel-titanium alloys (nitinol).

A problem with such stents is their limited bendability, particularly on introducing through narrow organs, such as blood vessels, at the point where a widening can take place. There is a risk that on bending the stent it bends in in the center as a result of the action of axially vertically directed forces, in that its cross-sectional area is reduced in the direction of the acting forces, but is widened perpendicular thereto and to the axial direction thereof. This can make insertion more difficult and can also damage the surrounding tissue, particularly if the stent is to be inserted in a bend area of the vessel or the like. Stents are relatively stiff and inflexible. This more particularly applies with stents having a rhombic structure, which are e.g. produced by cutting from nickel-titanium sheeting and have memory characteristics.

SUMMARY OF THE INVENTION

The problem of the invention is consequently to provide a stent, which has a high bending flexibility in the case of axially vertically acting forces and which is in particular subject to no deformations of its contour, particularly suffering no cross-sectional changes in the case of bending.

According to the invention this problem is solved by a stent, which is characterized in that it has several axially succeeding meander paths extending over its circumference, that between axially facing areas of the meander paths interconnected by connecting portions in the circumferential direction there are at least two facing, non-interconnected areas of each meander path.

Due to the fact that with such a stent and with several axially succeeding material paths guided in meander-like manner over the circumference facing or directed towards one another, adjacent areas of two adjacent meander paths are not interconnected in all cases, but instead between such interconnected areas there are circumferentially at least two non-interconnected areas, a higher flexibility is obtained than would be the case with a stent in which all the facing, adjacent areas of two adjacent meander paths were firmly interconnected. This not only leads to a higher flexibility, but it is in particular achieved that no cross-sectional deformation occurs at bends under the action of axially vertical forces.

An important advantage of the invention is that a high bendability is achieved without multilayer material crossing points, such as is the case in knitted, woven and braided structures. Due to the fact that there are no such material crossing points, the stent according to the invention grows better into the tissue. It also significantly reduces or eliminates the risk of the occurrence of thromboses, particularly in the vascular region.

According to a preferred development the connecting portions of axially succeeding meander paths are reciprocately displaced in the circumferential direction and in particular the connecting portions are circumferentially displaced by half a meander period, so that the desired axial strength is retained or obtained.

The meander paths can be formed in numerous different ways. Thus, according to preferred developments, the meander paths are zig-zag-like (with peaks), the meander paths are sinusoidal and that the meander paths have an oval construction. According to further preferred developments facing areas of the meander paths are aligned in the axial direction and/or that the width of the connecting areas in the circumferential direction is no larger than the width of the legs of the meander paths.

The stent is preferably self-expanding and is made from a memory metal material. In the low temperature state (well below body temperature), the individual meander legs engage with one another, whereas in the high temperature state (below but closer to body temperature) the stent is radially widened.

Further advantages and features of the invention can be gathered from the claims and the following description of the inventive stent with reference to the attached drawings.

BRIEF DESCRIPTION OF DRAWINGS

FIG. 1 is a preferred development of the stent according to the invention in its low temperature or insertion configuration.

FIG. 2 is the stent of FIG. 1 in its high temperature or positioning configuration.

FIG. 3 is a diagrammatic representation of a stent separated longitudinally at its welding positions and laid out flat in order to better illustrate the connection of the successive, axial, zig-zag meander paths.

DETAILED DESCRIPTION OF DISCLOSED EMBODIMENT

Figure 4:
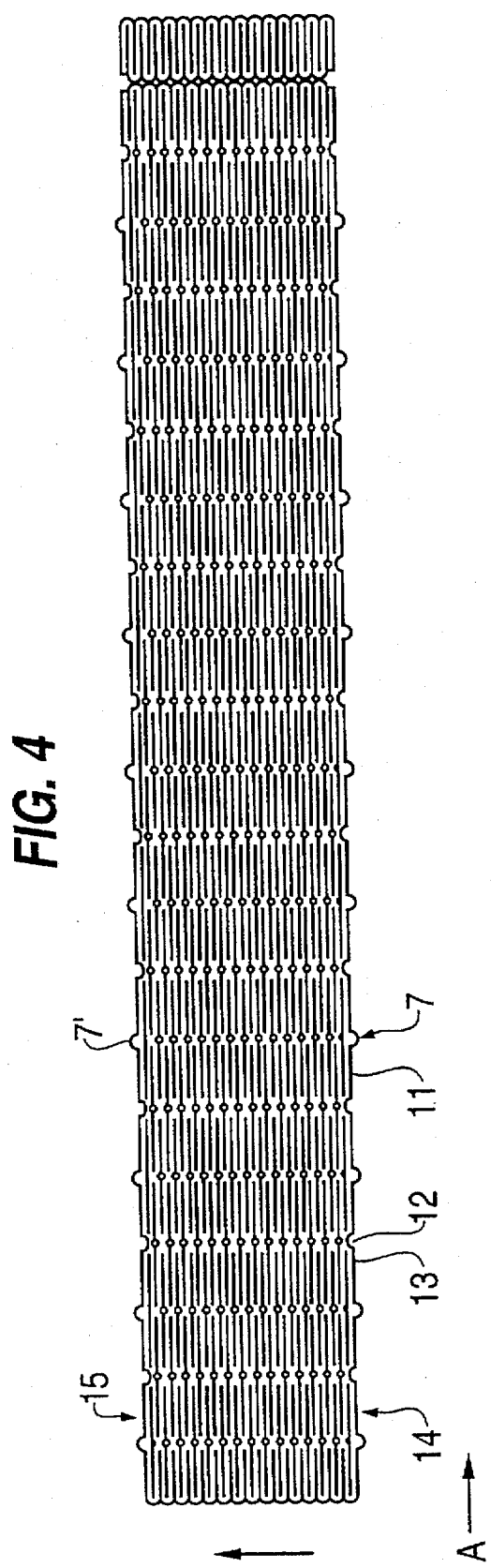
FIG. 4 is a slotted plate for producing a stent according to the invention.

In the represented embodiment the stent 1 according to the invention has a cylindrical shape, the outer contour of the stent being indicated by broken lines S in FIG. 2.

In place of a cylindrical design the stent 1 can also have a conical, biconical, frustum-shaped or other contour. It always has an axis of symmetry A, which determines the axial direction. The circumferential direction is indicated by the arrow U.

As can in particular be gathered from FIGS. 2 end 3, the stent 1 according to the invention comprises a number of meander paths 2, 2a, 2b succeeding one another in the axial direction A. In the circumferential direction the meander paths 2, 2a, 2b are arranged in such a way that in each case facing, adjacent peak areas 3, 3a or 3'a, 3b of in each case juxtaposed meander paths 2, 2a, 2b are axially aligned.

FIGS. 2 and 3 clearly show that not all the facing, adjacent peak areas 3, 3a, 3'a, 3b of the meander paths 2, 2a, 2b are interconnected by connecting areas 4, 4a, 4b, 4c, 4d, but between such connecting areas 4 to 4d of two adjacent meander paths 2, 2a are circumferentially provided several gaps 5, 5', 5a, 5b, 5b'. This leads to a high flexibility of the stent according to the invention. It is in particular achieved that when the stent 1 is bent at right angles to its longitudinal axis A the central area does not bend in in such a way that it loses its cross-sectionally, substantially circular contour and is pressed flat in the center in the action direction of the forces and perpendicular to the action direction of the forces is not widened in the center of its longitudinal extension as is the case with conventional stents, where all the facing, adjacent peak areas 3, 3a etc. of juxtaposed meander turns are firmly linked by connecting areas 4, 4a etc.

The connecting areas 4, 4a etc. are in one piece with the remaining part of the stent, particularly the meander paths 2, 2a etc. and their adjacent areas 3, 3a.

It can be gathered from FIG. 1 that the substantially rhombic free spaces formed between the legs of the meander paths 2,2a etc. in the high temperature setting taper to slots in the low temperature setting and the legs of the meander paths 2, etc. are substantially parallel to one another.

FIG. 3 also shows that the circumferential thickness of the connecting areas 4, 4a, 4b, 4c is no greater than the thickness of the individual legs of the meander paths 2, 2a, etc. The areas 7, 7' or 7a, 7a' are welded areas, which in the closed position of the stent shown in FIG. 3 are interconnected by welded joints.

FIG. 4 shows a slotted plate from which the stent according to the invention can be produced, The stent is made from a nickel-titanium alloy, such as nitinol. In a flat plate the openings or slots 11, as shown in FIG. 4, are produced in that circumferentially adjacent slots are in each case displaced by approximately half their length in the axial direction A. In the central area of each slot 11 the latter is provided with a widening 12, so that the material bounding the widening 12 in the circumferential direction is reduced roughly to the width of the material left between the slots. If the portions 13 are left, they later form the connecting portions 4, 4a, etc., or in the areas where the portions 13 are removed, the free spaces or gaps 5, 5a, etc. are created.

After producing the plate in the form shown in FIG. 4 initially all the portions 13 are left. Only to the left is it indicated in FIG. 4 how subsequently, i.e. after producing the stent, as shown in FIGS. 1 and 2, the separations are formed for creating the gaps 5.

The plate shown in FIG. 4 is bent to form a cylinder, so that the two edges 14,15 are in contact. At the welding points 7, 7' the welding joints are made and as a result initially a stent is formed in its low temperature position corresponding to FIG. 1. This is followed by a heat treatment, so as to give memory characteristics to the resulting stent, so that after raising the temperature to a predetermined ambient temperature, which is below the temperature of the human body, it can widen to its high temperature position corresponding to FIG. 2.

After producing and heat treating the stent in this way, the bridges 13 are removed in the desired manner, so that the connecting areas or webs 4, 4a, etc. or free spaces 5, 5', 5a, etc. are formed, in the manner described hereinbefore. In FIG. 3 between two circumferentially succeeding connecting areas or webs 4, 4a are in each case formed two free spaces 5 of adjacent, facing areas 3, 3a of the meander turns 2, 2a. The portions between the joining areas 4 in the circumferential direction can also be made larger. As a rule, there should be at least two free spaces 5 between two circumferentially succeeding webs 4.

The invention provides a highly flexible stent, which can follow all the bends without any deterioration.

We claim:

1. A stent comprising a plurality of succeeding meander paths, which succeed one another in an axial direction of said stent and extend over a circumference of said stent, each of said meander paths having legs which are connected with one another along their associated meander path by turns of said meander paths which form peaks of the meander paths in the axial direction, axially adjacent meander paths having oppositely directed peaks axially facing one another at a plurality of locations spaced about the circumference of the stent, which peaks are interconnected by connecting portions of the meander paths, and wherein between axially facing peaks, interconnected by said connecting portions, of the meander paths are provided in the circumferential direction two axially facing, non-interconnected peaks of each meander path which are closely spaced from corresponding peaks of the adjacent meander path by relatively small gaps to form a plurality of substantially closed free spaces between successive peaks in the circumferential direction.

2. Stent according to claim 1, wherein the connecting portions of axially succeeding meander paths are reciprocately displaced in the circumferential direction.

3. Stent according to claim 2, wherein the connecting portions are displaced by half a meander period in the circumferential direction.

4. Stent according to claim 1, wherein the meander paths have a zig-zag construction.

5. Stent according to claim 1, wherein the meander paths are sinusoidal.

6. Stent according to claim 1, wherein the meander paths are oval.

7. Stent according to claim 1, wherein the facing peaks of the adjacent meander paths are aligned in the axial direction.

8. Stent according to claim 1, wherein the width of the connecting areas in the circumferential direction is no greater than the width of the legs of the meander paths.

9. Method for producing a stent from a memory alloy, comprising making slots in a flat plate formed of a memory metal material in such a way that perpendicular to their extension direction adjacent slots are displaced by approximately half their length in the extension direction, bending the thus worked plate to form a cylinder with edges of the plate contacting each other, interconnecting contacting edges of said cylinder by welding at weld points and heat treating the welded cylinder to give the stent memory characteristics, so that after raising its temperature to above ambient temperature, but below the body temperature of the human body, it widens in a high temperature position.

10. Method according to claim 9, wherein in the central region of each slot the slot is provided with a widening, so that the material bounding the widening in the direction perpendicular to the extension direction of the slots roughly has the width of the material left between the slots.

11. Method according to claim 9 and 10, including forming welding areas on the lateral edges of the flat plate before bending said plate to form a cylinder, said welding areas being welded to interconnect the contacting edges after said bending of said plate.

12. Method according to claim 9, wherein each of said slots made in the flat plate defines a closed free space, and wherein after said slotted flat plate is bent and welded to form said welded cylinder, said method including in a plane perpendicular to the extension direction of the slots, partly removing webs left behind between two succeeding slots in the extension direction thereof so as to create free spaces or gaps extending between each of adjacent closed, free spaces in said plane.

13. Method according to claim 12, wherein free spaces or gaps are provided between at least two circumferentially following webs.

14. Method according to claim 12, wherein the webs are left in axially succeeding planes with a circumferential displacement.

15. A stent comprising a plurality of succeeding of meander paths, which succeed one another in an axial direction of said stent and extend over a circumference of said stent, each of said meander paths having legs which are connected with one another along their associated meander path by turns of said meander paths which form peaks of the meander paths in the axial direction, axially adjacent meander paths having oppositely directed peaks axially facing one another at a plurality of locations spaced about the circumference of the stent, which peaks are interconnected by connecting portions of the meander paths, and wherein between axially facing peaks interconnected by said connecting portions, of the meander paths are provided in the circumferential direction at least two axially facing non-interconnected peaks of each meander path which are closely spaced from corresponding peaks of the adjacent meander path by relatively small gaps to form a plurality of substantially closed free spaces between successive peaks in the circumferential direction, said stent being made by a method comprising making slots in a flat plate formed of a memory metal metal material in such a way that perpendicular to their extension direction adjacent slots are displaced by approximately half their length in the extension direction, bending the thus worked plate to form a cylinder with edges of the plate contacting each other, interconnecting contacting edges of said cylinder by welding at weld points and heat treating the welded cylinder to give the stent memory characteristics, so that after raising its temperature to above ambient temperature, but below the body temperature of the human body, it widens in a high temperature position, wherein each of said slots made in the flat plate defines a closed free space, and wherein after said slotted flat plate is bent and welded to form said welded cylinder, said method including in a plane perpendicular to the extension direction of the slots, partly removing webs left behind between two succeeding slots in the extension direction thereof so as to create said relatively small gaps extending between each of adjacent, closed free spaces in said plane.

16. A stent comprising a plurality of succeeding meander paths, which succeed one another in an axial direction of said stent and extend over a circumference of said stent, each of said meander paths having legs which are connected with one another along their associated meander path by turns of said meander paths which form peaks of the meander path in the axial direction, axially adjacent meander paths having oppositely directed peaks axially facing one another at a plurality of locations spaced about the circumference of the stent, which peaks are interconnected by connecting portions of the meander paths, and wherein between axially facing peaks, interconnected by said connecting portions, of the meander paths are provided in the circumferential direction at least two axially facing, non-interconnected peaks of each meander path which are closely spaced from corresponding peaks of the adjacent meander path by relatively small gaps to form a plurality of substantially closed free spaces between successive peaks in the circumferential direction.

* * * * *